United States Patent [19]

Dikeman

[11] 4,322,217
[45] Mar. 30, 1982

[54] PROCESS FOR PREPARING LIMULUS LYSATE

[75] Inventor: Roxane N. Dikeman, Creve Coeur, Mo.

[73] Assignee: Mallinckrodt, Inc., St. Louis, Mo.

[21] Appl. No.: 254,233

[22] Filed: Apr. 14, 1981

Related U.S. Application Data

[63] Continuation-in-part of Ser. No. 163,456, Jun. 27, 1980, abandoned.

[51] Int. Cl.³ ...................... G01N 31/00; G01N 33/00
[52] U.S. Cl. .................................. 23/230 B; 252/408; 435/7; 435/29
[58] Field of Search ...................... 23/230 B; 252/408; 435/4, 7, 29

[56] References Cited

U.S. PATENT DOCUMENTS

| | | | |
|---|---|---|---|
| 3,280,179 | 10/1966 | Ernst | 260/501 |
| 3,368,978 | 2/1968 | Irani | 252/137 |
| 3,539,521 | 11/1970 | Snoddy et al. | 252/137 |
| 3,915,805 | 10/1975 | Levin | 195/103.5 R |
| 3,954,663 | 5/1976 | Yamamoto et al. | 252/408 |
| 4,038,029 | 7/1977 | Teller et al. | 23/230 B |
| 4,096,091 | 6/1978 | Hopkins | 252/408 |
| 4,107,077 | 8/1978 | Sullivan, Jr. et al. | 252/408 |
| 4,273,557 | 6/1981 | Juranas | 23/230 B |

FOREIGN PATENT DOCUMENTS 1522127 8/1978 United Kingdom .
1530810 11/1978 United Kingdom .
2019563 10/1979 United Kingdom .
2033081 5/1980 United Kingdom .

OTHER PUBLICATIONS

Shands, Jr. et al., Journal of Biological Chemistry, vol. 255, No. 3, pp. 1221-1226, 1980.
Rudbach et al., Canadian Journal of Microbiology, vol. 14, pp. 1173-1178, 1968.
J. Sullivan and S. Watson, Applied Microbiology, vol. 28, No. 6, pp. 1023-1026, 1975.
G. W. Fernley, Journal of American Oil Chemists Society, vol. 55, pp. 98-103, 1978.
E. Hammecart-Pokorni et al, European Journal of Biochemistry, vol. 38, No. 1, pp. 6-13, 1973.
Levin and Bang, Thromb. Diath. Haemorrh, vol. 19, pp. 186-187, 1968.
Sweadner et al., Applied and Environmental Microbiology, vol. 34, No. 4, pp. 382-385, 1977.
McIntire et al., Biochemistry, vol. 8, No. 10, pp. 4063-4067, 1969.

Primary Examiner—Robert J. Warden
Attorney, Agent, or Firm—Roy J. Klostermann; L. N. Goodwin

[57] ABSTRACT

This invention relates to a process for treating Limulus Lysate having improved sensitivity to endotoxin, to lysate reagents utilizing such lysate, and to the use of such lysate reagents.

28 Claims, No Drawings

PROCESS FOR PREPARING LIMULUS LYSATE

This application is a continuation-in-part of application of Ser. No. 163,456 filed June 27, 1980 now abandoned.

This invention relates to a process for improving the sensitivity of Limulus amebocyte lysate (hereinafter sometimes referred to as LAL or lysate) to endotoxin, to an improved LAL reagent and to the use of such LAL reagent.

As is well known, the LAL test for detecting endotoxins is perhaps the most practical and sensitive test for determining endotoxins. Commercial assay tests employ amebocyte lysate from Limulus hemolymph obtained from the horseshoe crabs. This lysate is combined with appropriate divalent cations, appropriate buffers and other ingredients to form a LAL reagent. This reagent then reacts with endotoxin during the assay to form a gel. Manufacturers of LAL reagents often experience difficulty in producing lysate of the desired sensitivity for detecting endotoxin. Sensitivity from one preparation to the next is also variable. These problems are attributed at least in part to the presence of an endogenous, undefined endotoxin inhibitor substance in the lysate, (hereinafter sometimes referred to as the inhibitor).

Little is known of the nature of the inhibitor or its in-vivo role in the horseshoe crab. Electrophoretic studies indicate that the inhibitor is a high molecular weight lipoprotein. It may function in the amebocyte to control the coagulation defense mechanism. That the inhibitor may be a membrane component freed during cell lysis is also plausible. The uncertainty of the role and origin of the inhibitor is compounded by the fact that the mechanism of inhibition is unclear. The inhibitor presumably blocks the enzymatic reaction in some fashion either by association with the enzyme itself, or with the endotoxin or both. Like some other serine proteases, the proclotting enzyme is though to be complexed with calcium and glycerophospholipid. Endotoxin itself is lipoidal, hence, an inhibitor of lipoprotein character would be highly compatible with either component.

That the inhibitor is a lipoprotein is supported by its sensitivity to chloroform. As described in U.S. Pat. No. 4,107,077, the sensitivity of LAL is improved substantially when lysate is treated with an organic solvent such as chloroform to precipitate inhibitor from the lysate. The aqueous phase is then recovered and processed to prepare the LAL reagent.

To date, the above-mentioned solvent extraction procedure is the most rapid means of improving LAL sensitivity. Unfortunately, the method has several drawbacks. Because of the absolute requirement that endotoxin-free conditions be maintained throughout the lysate production, a cumbersome extraction procedure and subsequent centrification increases the likelihood of product failure. As noted in the patent, the solvent treatment reduces lysate stability such that the production must be completed rapidly in the cold. Also the precipitate removed from the lysate by the solvent treatment contains considerable coagulogen, the required clotting protein. Maintenance of adequate protein content is a requirement for firm gelation during endotoxin assay. Obviously, under the latter circumstances, control of reagent sensitivity is difficult. Chloroform, the solvent used most successfully, is well known for its undesirable effects in man. The health and safety of production personnel is therefore a reasonable concern. It is apparent that a process which avoids these pitfalls and yet improves sensitivity to the desired degree would be an improvement in the art.

It is therefore an object of the present invention to provide a method for the simple and rapid enhancement of the sensitivity of LAL.

In accordance with this invention, there is provided a process for treating under lysate treating conditions LAL having decreased sensitivity to endotoxin due to the presence of an endogenous inhibitor with an enhancing amount of a lysate sensitivity enhancing agent to neutralize or partially neutralize the lysate inhibitor thereby increasing the LAL sensitivity to endotoxin.

There are certain minimal criteria which can delineate LAL sensitivity enhancing characteristics, i.e., the LAL sensitivity enhancing agents useful in the process of this invention should possess (a) the ability to increase the lysate sensitivity to a suitable sensitivity, e.g., by a twofold or greater increase, (b) the ability to withstand depyrogenation, i.e. removal or destruction of endotoxin, by ultrafiltration or acid treatment at pH less than 5 or base treatment greater than pH 8, (c) the ability to be sterilized e.g., by autoclaving e.g. at or above 121° C. at 15 psi for 15 minutes, (d) the ability to form aqueous solutions of about 2% (w/v) at 25° C., (e) the ability to function in the pH range of about 6.0 to about 9, (f) the ability to be compatible with buffers and other ingredients utilized in the LAL reagent and (g) the ability to be compatible with respect to LAL and its reaction with endotoxins.

Such enhancing agents include amphoteric surfactants which have both an anionic and cationic group in their structure. Illustrative are the sulfobetaines represented by the following formula (hereinafter Formula A:

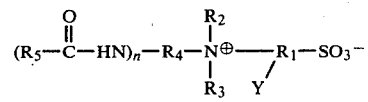

wherein:
R$_1$ is an alkylene radical having from 1 to about 4 carbon atoms,

Y is any non-deleterious, chemically suitable substituent including (1) hydrogen, (2) substituted or unsubstituted lower alkyl, e.g. containing 1 to 4 carbon atoms such as methyl, ethyl, propyl, or hydroxy etc.;

R$_2$ and R$_3$ are each selected from substituted or unsubstituted lower alkyl containing 1 to 4 carbon atoms, eg, such as methyl, ethyl, propyl, hydroxy ethyl, hydroxy methyl, hydroxy propyl, etc.

n=0 or 1, when n=0, R$_4$ is substituted or unsubstituted alkyl, e.g. containing about 8 to about 18 carbon atoms, when n=1, R$_4$ is an alkylene radical having from about 1 to about 6 carbon atoms, R$_5$ is a substituted or unsubstituted alkyl, eg containing about 8 to about 18 carbon atoms;

It is to be understood that the term "alkylene" as it is used herein, encompasses both polymethylene radicals and other divalent saturated aliphatic radicals and thus there may be branching in the linkage provided by the alkylene radical. The item "lower" means a radical containing 1 to 4 carbon atoms.

The sulfobetaines which are employed in the compositions of the present invention are known in the art and have been described as zwitterionic surfactants. The preparation of such compounds is described, for example, by G. W. Fernley in the JOURNAL OF AMERICAN OIL CHEMISTS SOCIETY, January 1978 (Vol. 55), pages 98–103, and by R. Ernst in the U.S. Pat. No. 3,280,179 issued Oct. 18, 1966, which patent is incorporated herein by reference.

In preferred sulfobetaine surfactants, $R_2$ and $R_3$ in the above structure are methyl. It is also prefered that $R_1$ be propylene.

One type of sulfobetaine surfactant which can be employed has the above structure wherein n equals 0 and $R_4$ is an alkyl radical having from about 8 to 18 carbon atoms, preferably a straight chain alkyl radical. For these sulfobetaine surfactants, a convenient source of the $R_4$ component is tallow fatty alcohol which consists of a mxture of various chain lengths, with a typical composition being approximately 66 percent $C_{18}$, 30 percent $C_{16}$ and 4 percent $C_{14}$ and others. Another convenient source is the middle cut of distilled coconut fatty alcohol, which also consists of a mixture of various chain lengths, with a typical composition being approximately 66 percent $C_{12}$, 23 percent $C_{14}$, 9 percent $C_{16}$ and 2 percent $C_{10}$.

Specific sulfobetaine surfactants of the above structure wherein n equals 0 are set forth in U.S. Patent 3,3539,521 issued on Nov. 10, 1970 to A. O. Snoddy et al, which patent is herein incorporated by reference. A surfactant of this type particularly preferred is N-tetradecyl-N,N-dimethyl-3-ammonio-1-propanesulfonate commercially available from Calbiochem-Behring Corporation under the trademark ZWITTERGENT 3-14.

Another type of sulfobetaine surfactant which can be employed has the above structure wherein n equals 1 and $R_4$ is an alkylene radical having from about 1 to about 6 carbon atoms. In these sulfobetaines wherein n equals 1, $R_5$ is an alkyl radical having from about 8 to about 18 carbon atoms. It is preferred that $R_5$ be straight chain. As previously discussed, convenient sources of alkyl radicals having from about 10 to about 18 carbon atoms are tallow fatty alcohol and coconut fatty alcohol.

Specific sulfobetaine surfactants of the above structure wherein n equals 1 are set forth in the previously mentioned U.S. Pat. 3,280,179.

Particularly preferred sulfobetaine surfactants for use in compositions of the present invention are 3-(N,N-dimethyl-N-acylamidopropylammonio)-2-hydroxypropane-1-sulfonates wherein the acyl group is derived from tallow fatty alcohol or coconut fatty alcohol, with coconut fatty alcohol preferred. It would be recognized by those skilled in the art that in the normal preparation of these derivatives of tallow or coconut fatty alcohols, a mixture of sulfobetaines with varying carbon chain lengths for the acyl groups would result. As previously discussed, these fatty alcohols contain for the most part carbon chain lengths which will provide acyl groups with the desired number of carbon atoms, that is from about 8 to about 18 carbon atoms. Thus, these mixtures obtained from tallow or coconut fatty alcohols are useful in providing the sulfobetaine surfactant in the compositions of the present invention. A material of this type particularly preferred for use in the composition of the present invention is N-cocoamido-propyl-N,N-dimethyl-N-2-hydroxypropyl sulfobetaine, an example of which is LONZAINE CS, commercially available from Lonza, Inc., Fair Lawn, N.J., another example of which is VARION CAS commercially available from Sherex Chemical Company, Inc.

Other amphoteric surfactants include, the N-long chain alkyl aminocarboxylic acids illustrated by the formula (hereafter Formula B):

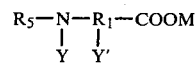

the N-long chain alkyl iminodicarboxylic acids illustrated by the formula (herinafter Formula C):

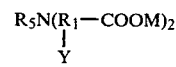

and the N-long chain alkyl or amido betaines illustrated by the formula (hereinafter Formula D):

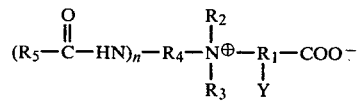

where $R_1$, $R_2$, $R_3$, $R_4$, Y and n have the same meaning as they have in Formula A, M is hydrogen or a salt-forming metal and Y' has the same meaning as Y in Formula A. Y and Y' may be the same or different. Examples of specific amphoteric detergents are N-alkylbeta-aminopropionic acid, N-alkyl-beta-iminodipropionic acid, and N-alkyl-N,N-dimethyl glycine; the alkyl group may be, for example, that derived from coco fatty alcohol, lauryl alcohol, myristyl alcohol (or a lauryl-myristyl mixture), hydrogenated tallow alcohol, cetyl, stearyl, or blends of such alcohols. The substituted aminopropionic and iminodipropionic acids are often supplied in the sodium or other salt forms, which may likewise used in the practice of this invention. Specific examples include cocobetaine sold by Witco Chemical Corporation under the name EMCOL CC 37–18; cocoamidopropyl betaine sold by Lonza Inc. and Sherex Chemical Company under the names LONZAINE CO and VARION CADG, respectively; sodium N-coco-beta-aminopropionate sold by Henkel Corporation under the name DERIPHAT 151; disodium N-lauryl-beta-iminodipropionate sold by Henkel Corporation under the name DERIPHAT 160, and disodium N-tallow-beta-iminodipropionate sold by Henkel Corporation under the name of DERIPHAT 154.

Examples of other amphoteric detergents are the fatty imidazolines such as those made by reacting a long chain fatty acid (e.g. of 10 to 20 carbon atoms) with diethylene triamine and monohalocarboxylic acids having 2 to 6 carbon atoms, e.g. 1-coco-5-hydroxyethyl-5-carboxymethylimidazoline.

Specific examples include cocoimidazoline commercially available under the name AMPHOTERGE K-2 from Lonza, Inc., capric dicarboxy imidazoline commercially available under the name AMPHOTERGE KJ2 from Lonza, Inc. and coco dicarboxy imidazoline blended with sulfated surfactants commercially available under the name AMPHOTERGE 2 WAS MOD from Lonza, Inc.

Other examples of enhancing agents include anionic synthetic surfactants, generally described as those compounds which contain hydrophilic and lipophilic groups in their molecular structure and ionize in an aqueous medium to give anions containing both the lipophilic group and hydrophilic group. The alkyl aryl sulfonates, the alkane sulfates and sulfated oxyethylated alkyl phenols are illustrative of the anionic type of surface active compounds.

The alkyl aryl sulfonates are a class of synthetic anionic surface active agents represented by the general formula (hereinafter Formula E):

$$(R_6)_{n_1}.(Y)Ar.(SO_3M)_{n_2}$$

$R_6$ is a straight or branched chain hydrocarbon radical having from about 1 to about 24 carbon atoms, at least one $R_6$ having at least 8 carbon atoms; $n_1$ is from 1 to 3; $n_2$ is from 1 to 2; Ar is a phenyl or a naphthyl radical and Y and M have the same meaning as in Formula B. $R_6$ can be, for example, methyl, ethyl, hexyl, octyl, tetraoctyl, iso-octyl, nonyl, decyl, dodecyl, octadecyl and the like.

Compound illustrative of the alkyl aryl sulfonates include sodium dodecylbenzene sulfonate, sodium decylbenzene sulfonate, ammonium methyl dodecylbenzene sulfonate, ammonium dodecylbenzene sulfonate, sodium octadecylbenzene sulfonate, sodium nonylbenzene sulfonate, sodium dodecylnaphthalene sulfonate, sodium hetadecylbenzene sulfonate, potassium eicososyl naphthalene sulfonate, ethylamine undecylnaphthalene sulfonate and sodium docosylnaphthalene sulfonate.

The alkyl sulfates are a class of synthetic anionic surface active agents represented by the general formula (hereinafter Formula F):

$$R_5OSO_3M$$

where $R_5$ and M have the same meaning as in Formula B.

Compounds illustrative of alkyl sulfate class of anionic surfactants include sodium octadecyl sulfate, sodium hexadecyl sulfate, sodium dodecyl sulfate, sodium nonyl sulfate, ammonium decyl sulfate, potassium tetradecyl sulfate, diethanolamino octyl sulfate, triethanolamine octadecyl sulfate and ammonium nonyl sulfate.

The sulfated oxyethylated alkylphenols are a class of synthetic anionic surface active agents represented by the general formula (hereinafter Formula G):

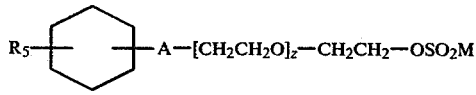

where A is either oxygen, sulfur, a carbonamide group, thiocarbonamide group, a carboxylic group or thiocarboxylic ester group, z is an integer from 3 to 8 and $R_5$ and M have the same meaning as in Formula B.

Compounds illustrative of the sulfated oxyethylated alkyl phenol class of anionic surfactants include ammonium nonylphenoxyl tetraethylenoxy sulfate, sodium dodecylphenoxy triethyleneoxy sulfate, ethanolamine decylphenoxy tetraethyleneoxy sulfate and potassium octylphenoxy triethyleneoxy sulfate.

Other examples of LAL enhancing agents include nonionic surface active compounds can be broadly described as compounds which do not ionize but acquire hydrophilic characteristics from an oxygenated side chain such as polyoxyethylene and the lipophilic part of the molecule may come from fatty acids, phenol, alcohols, amides or amines. The compounds are usually made by reacting an alkylene oxide such as ethylene oxide, butylene oxide, propylene oxide and the like, with fatty acids, straight or branched chain alcohols containing one or more hydroxyl groups, phenols, thiophenols, amides and amines to form polyoxyalkylene glycoethers and esters, polyoxyalkylene alkylphenols, polyoxyalkylene thiophenols, polyoxyalkylene amides and the like. It is generally preferred to react from about 3 to about 30, more preferably 10 to 30, moles of alkylene oxide per mole of the fatty acids, alcohols, phenols, thiophenols, amides or amines.

Illustrative of these nonionic surfactants are the products obtained from the reaction of alkylene oxide with an aliphatic alcohol having from 8 to 18 carbon atoms, such as octyl, nonyl, decyl, octadecyl, dodecyl, tetradecyl and the like; with monoesters of hexahydric alcohols, the ester group containing 10 to 20 carbon atoms such as sorbitan monolaureate, sorbitan monooleate and sorbitan monopalmitate; with an alkyl phenol in which the alkyl group contains between 4 and 20 carbon atoms, such as butyl, dibutyl, amyl, octyl, dodecyl, tetradecyl and the like; and with an alkyl amine in which the alkyl group contains between 1 to 8 carbon atoms.

Compounds illustrative of synthetic nonionic surfactants include the products obtained from condensing ethylene oxide or propylene oxide with the following: propylene glycol, ethylene diamine, diethylene glycol, dodecyl phenol, nonyl phenol, tetradecyl alcohol, N-octadecyl diethanolamide, N-dodecyl monoethanolamide, polyoxyethylene (20) sorbitan monooleate sold under the name TWEEN 80 and polyoxyethylene (20) sorbitan monolaurate sold under the name TWEEN 20.

Other nonionic surfactants include long chain tertiary amine oxides corresponding to the following general formula (hereinafter Formula H):

$$R_5R_7R_8N \rightarrow O,$$

wherein $R_5$ has the same meaning as in Formula A, and $R_7$ and $R_8$ are each methyl or ethyl radicals. The arrow in the formula is a conventional representation of a semi-polar bond. Examples of amine oxides suitable for use in this invention include dimethyldodecylamine oxide, dimethyloctylamine oxide, dimethyldecylamine oxide, dimethyltridecylamine oxide, dimethylhexadecylamine oxide.

Cationic surface active agents may also be employed as LAL enhancing agents. Such agents are those surface active compounds which contain an organic hydrophobic group and a cationic solubilizing group. Typical cationic solubilizing groups are amine and quaternary groups. Such cationic surface active agents are represented by the following general formula (hereinafter Formula I)

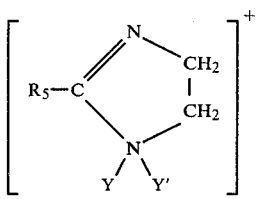

wherein $R_5$, Y and Y' have the same meaning as in Formula C. An example is QUATERNARY O available from Ciba-Geigy Corporation.

Other examples of suitable synthetic cationic surfactants include the diamines such as those of the formula (hereinafter Formula J):

$$R_9NHC_2H_4NH_2$$

wherein $R_9$ is an alkyl group of about 12 to 22 carbon atoms, such as N-2-aminoethyl stearyl amine and N-2-aminoethyl myristyl amine; amide-linked amines such as those of the formula (hereinafter Formula K):

$$R_5CONHC_2H_4NH_3$$

such as N-2-amino ethylstearyl amide and N-amino ethyl myristyl amide; quaternary ammonium compounds wherein typically one of the groups linked to the nitrogen atom are alkyl groups which contain 1 to 3 carbon atoms, including such 1 to 3 carbon alkyl groups bearing inert substitutents, such as phenyl groups and there is present an anion such as halogen, acetate, methylsulfate, etc. Typical quaternary ammonium compounds are ethyl-dimethylstearyl ammonium chloride, benzyl-dimethyl-stearyl ammonium chloride, benzyl-dimethyl-stearyl ammonium chloride, trimethyl stearyl ammonium chloride, trimethylcetyl ammonium bromide, dimethylethyl dilaurylammonium chloride, dimethyl-propyl-myristyl ammonium chloride, and the corresponding methosulfates and acetates.

Another suitable cationic surfactant is represented by the formula (hereinafter Formula L):

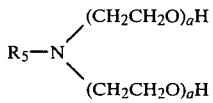

wherein $R_5$ has the same meaning as in Formula A and each a is an integer from 1 to 15. An example is the polyethylene glycol amine of hydrogenated tallow wherein $R_5$ represents the tallow radical and a+a has an average value of 5. It is available from Ciba-Geigy Corporation under the trade name BINA COBA 3001.

As mentioned, the lysate enhancing agent is used in enhancing amounts, i.e. sufficient to neutralize or partially neutralize the endogenous endotoxin inhibitor in the lysate. Generally, this is an amount from about 0.001 to 1.0% (w/v) preferably from about 0.01% to about 0.05% (w/v) based on the total volume of the lysate. Frequently, amounts in excess of an enhancing amount interfere with the ability of the LAL to react with endotoxin during assay.

LAL may be prepared by those procedures known in the art, e.g. the procedure, described in British Pat. No. 1,522,127 which is incorporated herein by reference.

For example, the hemolymph from healthy specimens of Limulus polyphemus is collected in a saline anticoagulant solution generally as described by Levin and Bang—"Clottable Protein in Limulus: Its Localization and Kinetics of Its Coagulation by Endotoxin", Thromb. Diath. Haemorrh. 19: 186-197 (1968).—The amebocytes are collected and washed with the saline anticoagulant solution with the amebocyte separated from the anticoagulant by centrifugation.

The separated amebocytes are suspended in water and the osmotic disruption of the cells is complemented by mechanical agitation. The cellular debris is separated from the lysate by centrifugation and the lysate fractions are pooled and stored at 0°-4° C.

To form the LAL reagent, the aforementioned LAL fractions are generally buffered to a suitable pH range, e.g. 5.5 to 8.5, preferably 6.5 7.5 by means of a suitable buffer, e.g. tris(hydroxymethyl)aminomethane, tris(hydroxymethyl)aminomethane maleate, 1,4-piperazinediethanesulfonic acid, morpholinopropanesulfonic acid, N-2-hydroxyethylpiperazine-N'-2-ethanesulfonic acid, triethanolamine, imidazole and tris(hydroxymethyl)imidazole. Then, the LAL reagent can be subdivided into serum vials, e.g. containing 1.2 or 5.2 ml. of solution and lyophilized. Normally, after lyophilization the vials are sealed and refrigerated (1°-5° C.).

Normally, in accordance with this invention the LAL is treated by adding the lysate sensitivity enhancing agent to the LAL after the LAL has been separated from the amebocyte cellular debris. Usually, it is added prior to or at the time of preparing the LAL reagent, e.g., simultaneously with the buffer and other ingredients.

Sensitivity of the LAL reagent toward endotoxin is further increased by including low concentrations of divalent and monovalent cations. Calcium and manganese ions are the preferred divalent ions, although other alkaline earth ions such as magnesium and strontium ions or other divalent ions may be used. Magnesium and strontium ions are also preferred divalent ions. Sodium ions are the preferred monovalent ions, but other monovalent ions, especially alkali metal ions such as lithium ions may be used. The chlorides ($CaCl_2$, NaCl, etc.) are convenient sources of these added ions, although other salts may be used. Preferably these electrolytes are added in endotoxin sensitivity increasing amounts, e.g. for the divalent cation (e.g., $Ca^{+2}$), the concentration will be in the range of 0.0001-0.4 molar and for the monovalent cation (e.g., $Na^+$), the concentration will be in the range of 0.01-0.4 molar.

The LAL reagent may also contain conventional adjuvants such as stabilizers, including lactose. These adjuvants when employed are provided in minor amounts sufficient to impart the intended qualities, but not adverse to, the desired properties of the LAL reagents.

All of the above operations are carried out under lysate treating conditions, which include insuring that the final product is sterile and free of endotoxin. Methods of insuring freedom from endotoxins are known to the art. For example, inorganic additives ($CaCl_2$, NaCl etc.) may be rendered endotoxin-free by heating the dry salts at 250° C. for at least 120 minutes. Organic additives, because of their melting points, etc., must ordinarily be dissolved, rendered acidic (pH<5) or alkaline (pH>9), and the solution autoclaved at 121° C. for 30-60 minutes or more to destroy any endotoxins present.

As mentioned, another aspect of the invention is directed to a LAL reagent containing as the essential ingredient an aqueous dispersion of LAL, a LAL sensitivity enhancing agent as described previously in a lysate enhancing amount and a suitable buffer described previously in a buffering amount. Optionally, monovalent and divalent cations described above can be included in lysate sensitivity increasing amounts to further increase the sensitivity of lysate to endotoxin.

Normally, the lysate in the reagent of this invention is present in an endotoxin determining amount, e.g. an amount sufficient to determine endotoxins in a subsequent LAL assay for endotoxins, and generally this is an amount that will detect about 0.007 to about 0.5 ng/ml, preferably from about 0.007 to about 0.050 ng/ml of FDA Reference Endotoxins EC-2. The aforementioned LAL reagent can be lyophilized which is preferred.

In accordance with this invention the LAL reagent can be utilized to determine endotoxin under endotoxin determining conditions according to the usual procedure, e.g. as described in British Pat. No. 1,522,127, and hereafter in the Examples.

The following examples illustrate the invention; all parts are by weight/volume unless otherwise stated.

PREPARATION OF LIMULUS LYSATE

Limulus Lysate was prepared by modification of a procedure described originally by Levin and Bang (Thromb. Diath. Haemorrh. 19. 186 (1969). Horseshoe crabs, *Limulus polyphemus*, were taken from the Atlantic Ocean in the vicinity of Beaufort, N.C. Hemolymph (approximately 500 ml) removed by cardiac puncture with a 16-gauge needle was collected in an endotoxin-free one liter glass centrifuge bottle which contained 500 ml of 0.125% N-ethylmaleimide in endotoxin-free 3% saline warmed to 42° C. The centrifuge bottle containing hemolymph-anticoagulant solution was warmed to 42° for 8 minutes and then centrifuged at 150×g for 10 minutes. The plasma supernatant was decanted and the amebocyte pellet was resuspended in anticoagulant solution. The cells were again pelleted by centrifugation as before. The packed cells were resuspended in 0.9% pyrogen-free saline and transferred to a depyrogenated 50 ml plastic centrifuge tube. The washed cells were centrifuged again at 150×g. After decanting the saline, the packed amebocytes were ruptured by addition of pyrogen-free water for injection in a ratio of 7 ml water to 3 ml packed cells. After mixing on a vortex for 10–15 seconds, the lysed cells were stored for 24 hours at 1°–5° C. Cell debris was sedimented by centrifugation at 1500×g for approximately 15 minutes. The lysate was decanted and stored at 0°–4° C. The cell debris was discarded.

PREPARATION OF STANDARD ENDOTOXIN SOLUTIONS

Standard solutions of Food and Drug Administration (FDA) reference standard endotoxin Lot EC-2 were prepared in pyrogen-free water for injection. Reconstitution of 1 µg endotoxin supplied in a vial with 10 ml water resulted in an initial concentration of 0.1 µg/ml. The vial was shaken on a reciprocal shaker for 1 hour. Serial dilutions were prepared to provide the following endotoxin concentrations: 10 ng/ml, 1 ng/ml, 500 pg/ml, 250 pg/ml, 125 pg/ml, 62.5 pg/ml, 31.25 pg/ml, 15.6 pg/ml, and 7.8 pg/ml. Once prepared, endotoxin solutions were stored up to 48 hours and then discarded. Other endotoxin standards used were solutions of FDA Reference Endotoxin Lot No. 1 from *Klebsiella pneumoniae*, *Escherichia coli* endotoxin Lot 071857 (Difco), and a reformulation of reference Lot EC-2 prepared in our laboratory. Endotoxin standard solutions prepared from E. coli Lot 071857 endotoxin were of the following concentrations: 6.25, 12.5, 50, 75, 100, 150, and 200 pg/ml.

LYSATE ASSAY PROCEDURE

Lysate dilutions of 25 to 70% were prepared in a 0.1 M buffer pH 7.0 which was usually tris, i.e., tris (hydroxymethyl)aminomethane. Other buffers used included imidazole, tris imidazole, triethanolamine, tris maleate, N-2-hydroxyethylpiperazine-N-2-ethanesulfonic acid (HEPES), 1,4-piperazinediethane sulfonic acid (PIPES), and morpholinopropane sulfonic acid (MOPS).

To determine the sensitivity of the lysate, 0.1 ml of each of the endotoxin dilutions was combined with 0.1 ml of lysate in depyrogenated 10×75 mm screw capped glass tubes and incubated for 1 hour at 37° C. Results were determined by gently inverting each tube to 180°. A clot which remained intact after the inversion indicated a positive endotoxin test.

PREPARATION AND DEPYROGENATION OF SURFACTANT SOLUTIONS

Stock LAL sensitivity enhancing agent solutions were prepared in concentrations up to 10% active ingredients in aqueous solution (w/v). Most frequently, the concentration prepared was 1% (w/v). Although the procedure varied in amounts from one agent to the next, enough material was dissolved in 50 ml aqueous solution to yield the desired concentration if diluted to 100 ml. The solution also contained 7.5 ml of 0.05 M tris(hydroxymethyl)aminomethane (i.e. TRIZMA BASE, Sigma Chemical Company) and 1 ml of 2 N NaOH to give a final pH $\geq$ 11. The agent in alkaline solution was stored for 12 hours or more at 0°–4° to insure complete depyrogenation. After adjusting the solution to approximately pH 8, it was autoclaved at $\geq$ 121° C. at 15 psi for 15 minutes or more. The pH was adjusted finally to pH 7.0±0.5. The agent concentration was calculated and the dilution adjusted to yield the final desired concentration. Alkali-labile agents were depyrogenated by acid treatment in which HCl and tris buffer were substituted for NaOH and TRIZMA BASE, respectively.

ADDITION OF AGENTS TO LYSATE

Agent solutions prepared as described above were added to the lysate during dilution with buffer. The amount added varied with the agent used, but the concentration range for all those tested was 0.001 to 1.0% (w/v) final concentration in the lysate solution. The order of addition of components did not alter the resulting lysate sensitivity.

EXAMPLE I

The LAL sensitivity enhancing agent, ZWITTERGENT TM 3-14, N,N-dimethyl-3-ammonio-1-propanesulfonate, a sulfobetaine sold by Calbiochem-Behring Corporation, was depyrogenated as described above and diluted to a final 1% concentration (w/v). Lysate lot 9CZC was prepared as a 50% dilution with 0.1 M tris-maleate buffer pH 7.0. Addition of the enhancing agent was carried out to yield final concentration in lysate of 0.005, 0.001, 0.02, 0.05, 0.075, and 0.10%

(w/v). A control sample contained pyrogen-free water instead of surfactant. The lysate dilutions were stored overnight at 0°–4° C. and tested the following day with a specially formulated EC endotoxin series of dilutions (designated EC). The results (Table I) indicate both the effective concentration range for enhancing agent and the total increase in lysate sensitivity to endotoxin as compare to the control lysate.

TABLE I

| Sample | Enhancing Agent (%) | Lysate Sensitivity* |
|---|---|---|
| Control | 0 | 500 |
| LAL plus | 0.005 | 1,000.0 |
| Enhancing Agent | 0.01 | 500.0 |
|  | 0.02 | 31.2 |
|  | 0.05 | 10,000.0 |
|  | 0.075 | 10,000.0 |
|  | 0.10 | 10,000.0 |

*Expressed as the lowest endotoxin concentration (pg/ml) which yields a positive clot test.

EXAMPLE II

Standard endotoxin solutions were prepared for *E. coli* endotoxin 071857, FDA Reference Endotoxin EC-2, and *K. pneumoniae* FDA reference Lot No. 1. Lysate was diluted with 0.1 M tris buffer pH 7.0 and the enhancing agent, ZWITTERGENT TM 3-14, solution to yield a 30% lysate dilution containing 0.02% ZWITTERGENT 3-14 (w/v). The agent was replaced by water in the control sample. The lysate assay was carried out with each endotoxin dilution series.

TABLE II

| Endotoxin | Sample | Lysate Sensitivity* |
|---|---|---|
| *E. coli* 071857 | Control | 75.0 |
|  | LAL enhancing agent | 25.0 |
| FDA Reference EC-2 | Control | 500.0 |
|  | LAL enhancing agent | 62.5 |
| FDA *K. pneumonia* | Control | 1,000.0 |
|  | LAL enhancing agent | 125.0 |

*Expressed as the lowest endotoxin concentration (pg/ml) which yields a positive clot test.

EXAMPLE III

Twenty-two commercially available LAL enhancing agents were surveyed to determine their effects on lysate sensitivity to endotoxin. Solutions of each were prepared and added to lysate Lot 9 FI in final concentrations ranging from 0.001 to 0.20% (w/v). Lysate samples were then tested with reformulated FDA EC endotoxin (EC). In Table III, the agents are listed in order of decreasing effectiveness. The most effective concentration tested in lysate and its corresponding lysate sensitivity are shown. The sensitivity of control lysate (50% dilution) containing no agent is also indicated.

TABLE III

| Trade Name | Source | Surfactant | Effective Concentration (%) | [a]Lysate Sensitivity |
|---|---|---|---|---|
| Zwittergent 3-14 | Calbiochem-Behring | Amphoteric | 0.02 | 15.6 |
| Varion CADG | Sherex Chemical Company, Inc. | Amphoteric | 0.02 | 15.6 |
| Lonzaine CO | Lonza Inc. | Amphoteric | 0.02 | 15.6 |
| Lonzaine CS | Lonza Inc. | Amphoteric | 0.02 | 15.6 |
| Varion CAS | Sherex Chemical Company, Inc. | Amphoteric | 0.02 | 31.2 |
| Emcol CC38-17 | Witco Chemical Corporation | Amphoteric | 0.02 | 31.2 |
| Deriphat 151 | Henkel Inc. USA | [b]Amphoteric | 0.01 | 31.2 |
| Bina Coba 3001 | Ciba-Geigy Corporation | Cationic | 0.01 | 31.2 |
| Barlox 12 | Lonza Inc. | Nonionic | 0.01 | 31.2 |
| Quaternary 0 | Ciba-Geigy Corporation | Cationic | 0.002 | 31.2 |
| Polystep B-5 | Stepan Chemical Company | Anionic | 0.001 | 31.2 |
| Tween 80 | ICI Americas Inc. | Nonionic | 0.20 | 62.5 |
| Amphoterge K-2 | Lonza Inc. | Amphoteric | 0.02 | 62.5 |
| Lodyne S-100 | Ciba-Geigy Corporation | Amphoteric | 0.02 | 62.5 |
| Deriphat 154 | Henkel Inc. USA | [b]Amphoteric | 0.002 | 62.5 |
| Polystep A-15 | Stepan Chemical Company | Anionic | 0.002 | 62.5 |
| Amphoterge KJ-2 | Lonza Inc. | Amphoteric | 0.001 | 62.5 |
| Deriphat 160 | Henkel Inc. USA | [b]Amphoteric | 0.02 | 62.5 |
| Polystep A-17 | Stepan Chemical Company | Anionic | 0.001 | 62.5 |
| Amphoterge WAS | Lonza Inc. | Amphoteric | 0.001 | 125.0 |
| Dianol RSX | Quaker Chemical Corporation | Anionic | 0.02 | 250.0 |
| Tween 20 | ICI Americas Inc. | Nonionic | 0.002 | 250.0 |
| Control Lysate | — | — | — | 125.0 |

[a]Expressed as the lowest endotoxin concentration (pg/ml) which yields a positive clot test.
[b]At pH 7, the anionic form predominates.

EXAMPLE IV

To determine that the increased sensitivity observed in lysate treated with the enhancing agent was maintained during lyophilization, 30% dilution of lysate in 0.05 M tris bufer with and without 0.02% ZWITTERGENT TM 3-14 (final concentration in lysate) were prepared. Lysate solution (1.2 ml) was dispensed into each 10-ml serum vial. Samples were frozen at −35° C. and lyophilized under 50μ vacuum with a drying time of approximately 32 hours. The vials were sealed with split rubber stoppers and metal caps. The freeze-dried lysate was reconstituted with 1.2 ml pyrogen-free water for injection and then tested with FDA Reference Endotoxin lot EC-2. Control lysate without the enhancing agent had a sensitivity of 62.5 pg/ml. In the presence of the enhancing agent, the sensitivity of the lysate was improved by twofold to 31.2 pg/ml.

EXAMPLE V

Limulus Lysate Day Pool Lot ODH approximately one week old was prepared as a 40% dilution in 0.05 M tris(hydroxymethyl) aminomethane maleate buffer, pH 7.0, containing in final concentrations 0.06 M $CaCl_2$ and 0.01 M $MnCl_2$ and 0.03% ZWITTERGENT TM 3-14. This solution was dispensed as 1.2 ml aliquots into 8 ml vials and frozen at −45° C. and lyophilized under 50 u vacuum with a drying time of approximately 28 hours. The vials were sealed with split rubber stoppers and capped with plastic screw caps. The freeze dried lysate was reconstituted with 1.2 ml pyrogen-free water for injection and tested with FDA Reference Endotoxin lot EC-2. Sensitivity of enhancing agent treated lyophilized lysate was 62 pg/ml. A control 40% dilution of LAL without enhancing agent tested before lyophilization had a sensitivity of 1 ng/ml.

EXAMPLE VI

Limulus Lysate Day Pools of a sensitivity equal to or greater than 500 pg/ml E. coli endotoxin 1CF were combined and prepared as a 40% dilution in 0.025 M tris(hydroxymethyl) aminomethane maleate buffer, pH 7.0, containing in final concentrations 0.02 M $MgCl_2$, 0.01 M $SrCl_2$, 0.01 M $CaCl_2$, and 0.025% ZWITTERGENT TM 3-14. This solution was dispensed in 1.2 ml and 5.2 ml aliquots in 10 ml vials and frozen at $-50°$ C. The samples were lyophilized under 100μ vacuum with a drying time of approximately 72 hours. The lyophilized product was reconstituted with 1.2 ml or 5.2 ml pyrogen-free Water for Injection depending on the starting volume of lysate. When tested with E. coli endotoxin 1CF following lyophilization, the sensitivity of the enhancing agent treated lyophilized lysate for both sample sizes was 25 pg/ml in comparison to the control sensitivity of 500 pg/ml.

What is claimed:

1. A process for treating under lysate treating conditions Limulus amebocyte lysate having decreased sensitivity to endotoxin due to the presence of an endogenous lysate inhibitor prior to any subsequent reaction with endotoxin with an enhancing amount of a lysate sensitivity enhancing agent having lysate sensitivity enhancing characteristics to neutralize or partially neutralize said lysate inhibitor thereby increasing the lysate sensitivity to endotoxin, said lysate enhancing agent being selected from the group consisting of (I) amphoteric surfactants having the following formulae:

$$(R_5-\overset{O}{\overset{\|}{C}}-HN)_n-R_4-\overset{R_2}{\underset{R_3}{\overset{|}{N^\oplus}}}-R_1-SO_3^\ominus \quad (A)$$
$$\qquad\qquad\qquad\qquad\qquad Y$$

$$R_5-\underset{Y}{\overset{|}{N}}-R_1-COOM \quad (B)$$
$$\qquad\quad Y'$$

$$R_5N(R_1-COOM)_2 \quad (C)$$
$$\quad\, \overset{|}{Y}$$

$$(R_5-\overset{O}{\overset{\|}{C}}-HN)_n-R_4-\overset{R_2}{\underset{R_3}{\overset{|}{N^\oplus}}}-R_1-COO^\ominus \quad (D)$$
$$\qquad\qquad\qquad\qquad\qquad Y$$

wherein
$R_1$ is an alkylene radical having from 1 to 4 carbon atoms;
Y and Y' are each (1) hydrogen, (2) lower alkyl or (3) hydroxy lower alkyl;
$R_2$ and $R_3$ are each (1) lower alkyl or (2) hydroxy lower alkyl;
n is 0 or 1, when n is 0, $R_4$ is alkyl containing from about 8 to about 18 carbon atoms;
when n is 1, $R_4$ is an alkylene radical having from 1 to about 6 carbon atoms;
$R_5$ is an alkyl containing from about 8 to about 18 carbon atoms;
M is hydrogen, sodium, potassium or ammonium;

(II) anionic surfactants have the following formulae:

$$(R_6)_{n_1}\text{-}(Y)Ar.(SO_3M)_{n_2} \quad (E)$$

$$R_5OSO_3M \quad (F)$$

wherein
$R_5$, Y and M have the same meaning as set forth above
$R_6$ is an alkyl from 8 to 24 carbon atoms
$n_1$ is an integer from 1 to 3
$n_2$ is 1 or 2
Ar is phenyl or naphthyl;

(III) cationic surfactants having the following formula:

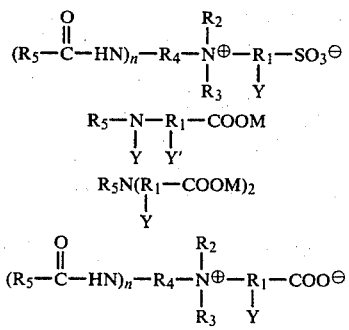

wherein
$R_5$, Y and Y' have the same meaning as set forth above; and (IV) nonionic surfactants having the following formula:

$$R_5R_7R_8N\rightarrow O \quad (H)$$

wherein
$R_5$ has the same meaning as set forth above
$R_7$ and $R_8$ are each methyl or ethyl; and those nonionic surfactants selected from the group consisting of the condensation product of about 10 to 30 moles of ethylene oxide with the monoester of a hexahydric alcohol containing 6 carbon atoms with the ester group containing 10 to 20 carbon atoms.

2. A process according to claim 1, wherein the enhancing agent is selected from the group of amphoteric surfactants represented by formula (A) of Claim 1.

3. A process according to claim 2, wherein the enhancing agent is present in an amount from about 0.01 to about 0.05% (w/v).

4. A process according to claim 3, wherein n is 0, $R_4$ is tetradecyl, $R_2$ and $R_3$ are each methyl, and $RY_1$ is trimethylene.

5. A process according to claim 3, wherein n is 1, $R_4$ is trimethylene, $R_2$ and $R_3$ are each methyl and $$R_1 \text{ is } -CH_2-\underset{Y}{\overset{|}{C}H}-\underset{OH}{\overset{|}{C}H_2}$$

6. A process according to claim 1, wherein the enhancing agent is selected from the group of amphoteric surfactants represented by formula (D) of claim 1.

7. A process according to claim 6, wherein the enhancing agent is present in an amount of from about 0.01 to about 0.05% (w/v).

8. A process according to claim 7, wherein n is 1, $R_4$ is propylene, $R_2$ and $R_3$ are each methyl and $$\overset{R_1}{\underset{Y}{|}}$$

is methylene.

9. A process according to claim 7, wherein n is 0, $R_2$ and $R_3$ are each methyl and $$\begin{matrix} R_1 \\ | \\ Y \end{matrix}$$

is methylene.

10. A Limulus ambeocyte lysate reagent for determining endotoxin by the formation of an intact clot comprising a buffered aqueous dispersion of Limulus amebocyte lysate present in an endotoxin determining amount having improved sensitivity to endotoxin and an enhancing amount of a lysate sensitivity enhancing agent having lysate sensitivity enhancing characteristics, said lysate enhancing agent being selected from the group consisting of (I) amphoteric surfactants having the following formulae:

(A) $(R_5\overset{O}{\overset{\|}{C}}-HN)_n-R_4-\overset{R_2}{\underset{R_3}{\overset{|}{N^\oplus}}}-R_1-SO_3^\ominus$ (B) $R_5-\underset{Y}{\overset{|}{N}}-R_1-COOM$
     $\phantom{R_5-N-}\underset{Y'}{|}$ (C) $R_5N(R_1 COOM)_2$
     $\phantom{R_5}\underset{Y}{|}$ (D) $(R_5-\overset{O}{\overset{\|}{C}}-HN)_n-R_4-\overset{R_2}{\underset{\underset{Y}{|}}{\overset{|}{\underset{R_3}{N^\oplus}}}}-R_1-COO^\ominus$ wherein
  $R_1$ is an alkylene radical having from 1 to 4 carbon atoms;
  Y and Y' are each (1) hydrogen, (2) lower alkyl or (3) hydroxy lower alkyl;
  $R_2$ and $R_3$ are each (1) lower alkyl or (2) hydroxy lower alkyl;
  n is 0 or 1, when n is 0, $R_4$ is alkyl containing from about 8 to about 18 carbon atoms;
  when n is 1, $R_4$ is an alkylene radical having from 1 to about 6 carbon atoms;
  $R_5$ is an alkyl containing from about 8 to about 18 carbon atoms;
  M is hydrogen, sodium, potassium or ammonium;
(II) anionic surfactants have the following formulae:

(E) $(R_6)_{n1}\text{-}(Y)Ar\text{-}(SO_3M)_{n2}$ (F) $R_5OSO_3M$ wherein
  $R_5$, Y and M have the same meaning as set forth above
  $R_6$ is an alkyl from 8 to 24 carbon atoms
  $n_1$ is an integer from 1 to 3
  $n_2$ is 1 or 2
  Ar is phenyl or naphthyl;
(III) cationic surfactants having the following formula:

(G) $\left[\begin{matrix} R_5-C\overset{\diagup N\diagdown}{\phantom{X}}\overset{CH_2}{\underset{CH_2}{|}} \\ \phantom{xx}\diagdown N \diagup \\ \phantom{xxx}Y\phantom{x}Y' \end{matrix}\right]^+$ wherein
  $R_5$, Y and Y' have the same meaning as set forth above; and
(IV) nonionic surfactants having the following formula:

$R_5R_7R_8N\rightarrow O$           (H)

wherein
  $R_5$ has the same meaning as set forth above
  $R_7$ and $R_8$ are each methyl or ethyl; and the nonionic surfactants selected from the group consisting of the condensation product of about 10 to 30 moles of ethylene oxide with the monoester of a hexahydric alcohol containing 6 carbon atoms with the ester group containing 10 to 20 carbon atoms.

11. A reagent according to claim 10, wherein additionally are present the cations, $Na^+$, $Mn^{++}$ and $Ca^{++}$ in lysate sensitivity increasing amounts.

12. A reagent according to claim 11, wherein the Lysate is present in an amount to detect from about 0.007 to about 0.050 ng/ml of FDA reference endotoxin EC-2.

13. A reagent according to claim 12, wherein the enhancing agent is selected from the group of amphoteric surfactants represented by formula A of claim 10.

14. A reagent according to claim 13, wherein n is 0, $R_4$ is tetradecyl, $R_2$ and $R_3$ are each methyl and $$\begin{matrix} R_1 \\ | \\ Y \end{matrix}$$

is trimethylene.

15. A reagent according to claim 13, wherein n is 1, $R_4$ is trimethylene, $R_2$ and $R_3$ are each methyl and $R_1$ is $-CH_2-\underset{\underset{Y}{|}}{CH}-\underset{\underset{OH}{|}}{CH_2}$ 16. A reagent according to claim 12, wherein the enhancing agent is selected from the group of amphoteric surfactants represented by formula D of claim 10.

17. A reagent according to claim 16, wherein n is 1, $R_4$ is propylene, $R_2$ and $R_3$ are each methyl and $$\begin{matrix} R_1 \\ | \\ Y \end{matrix}$$

is methylene.

18. A reagent according to claim 16, wherein n is 0, $R_2$ and $R_3$ are each methyl and $$\begin{matrix} R_1 \\ | \\ Y \end{matrix}$$

is methylene.

19. A reagent according to claim 10 which is lyophilized.

20. In a method for determining endotoxin under endotoxin determining conditions wherein the endotoxin is reacted with a Limulus amebocyte lysate reagent, the improvement comprising utilizing the Limulus amebocyte lysate reagent of claim 10.

21. A reagent according to claim 10, wherein additionally are present the cations, $Na^+$, $Sr^{++}$, $Ca^{++}$ and $Mg^{++}$ in lysate sensitivity increasing amounts.

22. A reagent according to claim 21, wherein the Lysate is present in an amount to detect from about 0.007 to about 0.050 ng/ml of FDA reference endotoxin EC-2.

23. A reagent according to claim 22, wherein the enhancing agent is selected from the group of amphoteric surfactants represented by forumla A of claim 10.

24. A reagent according to claim 23, wherein n is 0, $R_4$ is tetradecyl, $R_2$ and $R_3$ are each methyl and $$\begin{array}{c} R_1 \\ | \\ Y \end{array}$$

is trimethylene.

25. A reagent according to claim 23, wherein n is 1, $R_4$ is trimethylene, $R_2$ and $R_3$ are each methyl and $$R_1 \text{ is } -CH_2-\underset{\underset{OH}{|}}{CH}-CH_2-\underset{\underset{Y}{|}}{}$$

26. A reagent according to claim 21, wherein the enhancing agent is selected from the group of amphoteric surfactants represented by formula D of claim 10.

27. A reagent according to claim 26, wherein n is 1, $R_4$ is propylene, $R_2$ and $R_3$ are each methyl and $$\begin{array}{c} R_1 \\ | \\ Y \end{array}$$

is methylene.

28. A reagent according to claim 26, wherein n is 0, $R_2$ and $R_3$ are each methyl and $$\begin{array}{c} R_1 \\ | \\ Y \end{array}$$

is methylene.

UNITED STATES PATENT AND TRADEMARK OFFICE
CERTIFICATE OF CORRECTION

PATENT NO. : 4,322,217

DATED : March 30, 1982

INVENTOR(S) : Roxane N. Dikeman

It is certified that error appears in the above-identified patent and that said Letters Patent are hereby corrected as shown below:

Col. 1, line 2, "of" should be deleted ---

Col. 1, line 40, "though" should read thought ---

Col. 3, line 21, "mxture" should read mixture ---

Col. 7, line 34, "dimethylstearyl" should read dimethyl-stearyl ---

Col. 8, line 16, "6.5 7.5" should read 6.5 to 7.5 ---

Col. 10, line 38, "pH$\geq$" should read pH$\geq$ ---

Col. 10, line 42, "$\geq$ 121" should read $\geq$ 121 ---

Col. 10, line 68, "0.001" should read -- 0.01 --

Col. 12, line 45, "bufer" should read buffer ---

Col. 14, line 48, "RY$_1$" should read $\begin{array}{c}R\\|1\\Y\end{array}$ ---

UNITED STATES PATENT AND TRADEMARK OFFICE
CERTIFICATE OF CORRECTION

PATENT NO. : 4,322,217

DATED : March 30, 1982

INVENTOR(S) : Roxane N. Dikeman

It is certified that error appears in the above—identified patent and that said Letters Patent is hereby corrected as shown below:

Column 15, line 27, "$-R_1$" should read -- $R_1 \atop {\mid \atop Y}$ --.

[SEAL]

Attest:

Signed and Sealed this

Twenty-second Day of June 1982

*Attesting Officer*

GERALD J. MOSSINGHOFF

*Commissioner of Patents and Trademarks*